(12) United States Patent
Oyadiran et al.

(10) Patent No.: US 12,295,546 B2
(45) Date of Patent: May 13, 2025

(54) EAR AILMENT DIAGNOSTIC DEVICE AND METHOD

(71) Applicant: Zipline Health, Inc., San Francisco, CA (US)

(72) Inventors: Olabisi Oyadiran, Miramar, FL (US); Windell Roach, Virginia Beach, VA (US)

(73) Assignee: Zipline Health, Inc, San Francisco, CA (US)

( * ) Notice: Subject to any disclaimer, the term of this patent is extended or adjusted under 35 U.S.C. 154(b) by 118 days.

(21) Appl. No.: 17/951,750

(22) Filed: Sep. 23, 2022

(65) Prior Publication Data

US 2023/0255445 A1    Aug. 17, 2023

Related U.S. Application Data

(63) Continuation of application No. 16/590,148, filed on Oct. 1, 2019, now Pat. No. 11,471,035, which is a
(Continued)

(51) Int. Cl.
*A61B 1/227* (2006.01)
*A61B 1/00* (2006.01)
(Continued)

(52) U.S. Cl.
CPC ...... *A61B 1/00016* (2013.01); *A61B 1/00009* (2013.01); *A61B 1/00105* (2013.01); *A61B 1/00114* (2013.01); *A61B 1/00119* (2013.01); *A61B 1/00128* (2013.01); *A61B 1/015* (2013.01); *A61B 1/045* (2013.01);
(Continued)

(58) Field of Classification Search
CPC ............ A61B 1/00016; A61B 1/00009; A61B 1/00105; A61B 1/00114; A61B 1/00119; A61B 1/00128; A61B 1/015; A61B 1/045; A61B 1/0684; A61B 1/227; A61B 1/2275;
(Continued)

(56) References Cited

U.S. PATENT DOCUMENTS 5,527,261 A * 6/1996 Monroe .................... A61B 1/05
600/172
5,919,130 A * 7/1999 Monroe ................. A61B 1/042
600/156
(Continued)

*Primary Examiner* — Tessa M Matthews
*Assistant Examiner* — David C Comstock
(74) *Attorney, Agent, or Firm* — Foley Hoag LLP; John Lanza

(57) ABSTRACT

An ear ailment diagnostic device includes an ear piece, a light source, a magnification lens, an air conduction channel and a miniature digital camera, which is capable of taking still or digital images. The earpieces may optionally comprise a thermometer and/or tympanometer. Each earpiece is coupled to an air conduction tube, an insufflator and an electrical wiring/data tube which is coupled to a computer. The insufflator may be manually, electronically, or battery powered. In the preferred embodiment the computer comprises a smart phone with data processing capability and wireless communication capability. Any data sent from the device can then be interpreted and diagnosed in a remote location so that an accurate treatment is prescribed.

19 Claims, 3 Drawing Sheets

Related U.S. Application Data continuation of application No. 15/913,280, filed on Mar. 6, 2018, now Pat. No. 10,463,241, which is a continuation of application No. 15/214,329, filed on Jul. 19, 2016, now abandoned, which is a continuation of application No. 14/484,448, filed on Sep. 12, 2014, now abandoned, which is a continuation of application No. 13/031,233, filed on Feb. 20, 2011, now Pat. No. 8,858,430.

(60) Provisional application No. 61/311,813, filed on Mar. 9, 2010.

(51) Int. Cl.
*A61B 1/015* (2006.01)
*A61B 1/045* (2006.01)
*A61B 1/06* (2006.01)
*A61B 5/00* (2006.01)
*A61B 5/01* (2006.01)
*A61B 5/12* (2006.01)

(52) U.S. Cl.
CPC ............ *A61B 1/0684* (2013.01); *A61B 1/227* (2013.01); *A61B 1/2275* (2013.01); *A61B 5/0084* (2013.01); *A61B 5/01* (2013.01); *A61B 5/12* (2013.01); *A61B 5/126* (2013.01); *A61B 5/6898* (2013.01); *A61B 5/7405* (2013.01)

(58) Field of Classification Search
CPC ........... A61B 5/0084; A61B 5/01; A61B 5/12; A61B 5/126; A61B 5/6898; A61B 5/7405
USPC .......................................................... 600/200
See application file for complete search history.

(56) References Cited

U.S. PATENT DOCUMENTS 6,319,199 B1 * 11/2001 Sheehan ................ A61B 1/227
  600/184
2002/0038076 A1 * 3/2002 Sheehan ................ A61B 1/227
  600/200

* cited by examiner

EAR AILMENT DIAGNOSTIC DEVICE AND METHOD

CROSS REFERENCE TO RELATED APPLICATIONS

This application is a continuation of U.S. application Ser. No. 16/590,148, filed on Oct. 1, 2019 (now U.S. Pat. No. 11,471,035), which is a continuation of U.S. application Ser. No. 15/913,280 filed on Mar. 6, 2018 (now U.S. Pat. No. 10,463,241), which is a continuation of U.S. application Ser. No. 15/214,329, filed Jul. 19, 2016 (now abandoned), which is a continuation of U.S. application Ser. No. 14/484,448, filed Sep. 12, 2014 (now abandoned), which is a continuation of U.S. application Ser. No. 13/031,233, filed Feb. 20, 2011 (now U.S. Pat. No. 8,858,430), which claims the benefit of 35 U.S.C. § 119 and the filing date of U.S. provisional application No. 61/311,813, filed Mar. 9, 2010, each of which is incorporated by reference in its entirety.

FIELD OF INVENTION

The present invention relates to the field of medical devices. More specifically, the invention relates to medical devices and methods for the diagnosis of ear ailments.

FIELD OF INVENTION

Presently, the standard method of treatment for diagnosing external and middle ear infections requires a live in-person physician appointment and consultation. This is necessary for both the actual examination as well as for the diagnosis and management of a care plan. The patient usually must make an appointment, wait and eventually commute to the doctor's office; all of which takes a great deal of time and prolongs any potential injury.

A doctor will usually use an assortment of various test equipment such as thermometers, otoscopes, insufflators and tympanometers to diagnose the ailment. Thermometer readings can indicate if there is increased blood flow to the area due to inflammation or infection. Otoscopes, which typically include a light source and possibly a magnification lens, are commonly used to get a visual of the ear canal as well as test the mobility of the tympanic membrane (eardrum) by shooting a puff of air into the ear. The air can be powered electrically or manually by the use of a small bulb and tubing. Tympanometers or audiometers, which usually include headphones and a hardware circuit, can then be used to measure and diagnose the mobility of the eardrum and ossicles (conductive bones). The sound reflected back to this instrument can be used to diagnose otitis of the middle or external ear. The results of this test can also be graphed as a function of decibels over air pressure. The graphs can then be compared against the norm to reveal potential injuries such as perforation or scarring of the eardrum, buildup of wax or lack of contact between the conduction bones.

The presently disclosed device allows a patient to benefit from accurate and effective diagnosis of ear ailments through self examination and remote diagnosis. In this way, both time and expense are salvaged and lead to quicker diagnosis, which in effect can lead to faster recovery, healing and/or treatment.

SUMMARY OF THE INVENTION

An ear ailment diagnostic device and method in accordance with the present disclosure generally comprises at least one earpiece, which further comprise a light source, a magnification lens, an air conduction channel and a miniature digital camera, which is capable of taking still or digital images. The earpiece may optionally comprise a thermometer and/or tympanometer. The earpiece is coupled to an air conduction tube, an insufflator and an electrical/data wire which is coupled to a computer. The insufflator may be manually, electronically, or battery powered. The electrical wiring transmits power and video data between the camera and computer, and power and audio data between the tympanometer and computer. In the preferred embodiment the computer comprises a smart phone with data processing capability and wireless communication capability. Broadly, the preferred embodiment of the present disclosure generally provides for a telemedicine integrated compact device for the remote diagnosis and management of an assortment of ear ailments, especially of the external and middle ear.

One method of using the device comprises the steps of inputting user specific data, inserting at least one earpiece into at least one ear, positioning the earpiece and securing with a clip. Next, the user will set-up and activate the camera to capture an image or video, and transmit that data to a hospital, physician or data center. Any data sent from the device can then be interpreted and diagnosed in a remote location so that an accurate treatment is prescribed and sent back to the user. In another interactive embodiment of the method of using the device, the computer may generate a questionnaire for the user to fill out based on demographics, genetics or past medical history.

DETAILED DESCRIPTION OF THE PREFERRED EMBODIMENT

In the following description of the various embodiments, reference is made to the accompanying drawings, which form a part hereof, and in which is shown by way of illustration, various embodiments in which the invention may be practiced. It is to be understood that other embodiments may still be utilized and structural and functional modifications may be made without departing from the scope and spirit of the present invention.

Figure 1:
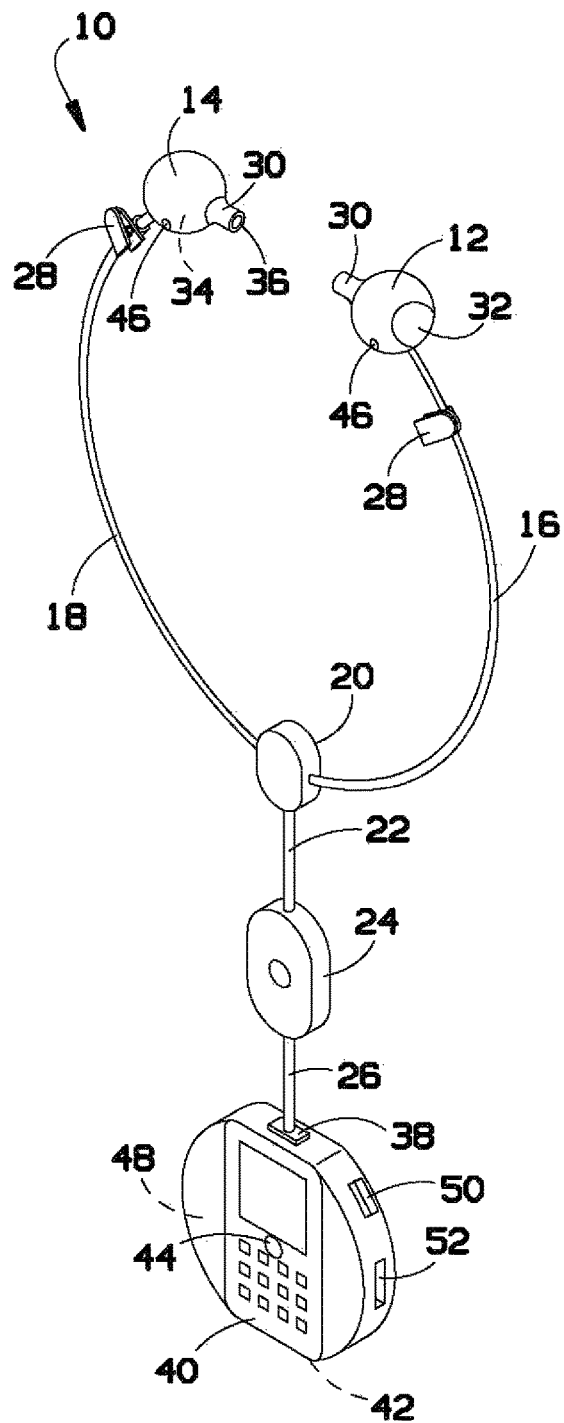
FIG. 1 illustrates a perspective view of the preferred embodiment of the present invention.

Referring to FIG. 1, a perspective view of the preferred embodiment of an ear ailment diagnostic device 10 is shown. In this preferred embodiment of ear diagnostic device 10, left earpiece 12 and right earpiece 14 are bulbous containers which house smaller components. Each earpiece, 12, 14 could alternatively take other similarly functional shapes but must comprise at least one tip 30 which is capable of fitting into the exterior of an ear canal. Both the earpieces, 12, 14 and tips 30 may swivel or pivot or be maneuverable, extendable, flexible or moldable so as to reach different areas and/or make a more secure connection. Each may further comprise a small protective shield which may be used to focus the light emanating from light source 32, which preferably is opposite tips 30 on earpieces 12, 14. Besides acting as visible conduit into the ear, tips 30 also comprise air tubes 36. Air tubes 36 may be straight down the middle of tips 30 or alternatively may be ring-shaped just inside the circumference edges of tips 30. In this latter shape they can function without impinging upon visibility and sound transmission. Each earpiece, 12, 14 will also comprise a miniature camera 34, preferably located inside the bulbous or spherical structure. Cameras 34 may be directly connected to earpieces 12, 14 or may form an extension of device 10 in some embodiments of the disclosure. Each camera may be adjustable so that it may focus on different areas within the first five millimeters of an ear canal. It may further include servos to remotely control its position, focus, magnification, aperture speed and independent lighting source for constant or flash lighting. Camera 34 may use any light source known in the art which is deemed appropriate for high quality still or motion pictures. A short motion picture or video clip, typically no more than fifteen seconds, may be stored on digital memory. Ear device 10 additionally comprises power button and LED power indicator lights 46, which may be located directly on earpieces 12, 14 as shown in FIG. 1, on any other part of device 10, or in a foreign location such as a remote controller.

Figure 2:
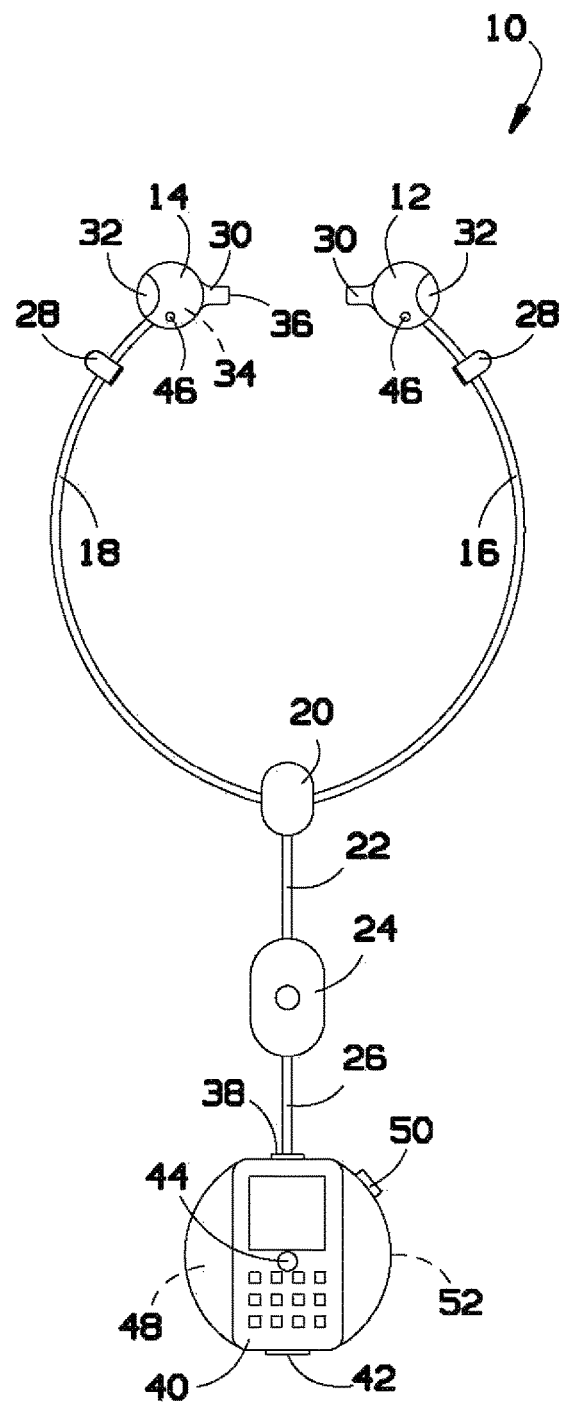
FIG. 2 illustrates a front view of the preferred embodiment of the present invention.

Now referring to FIG. 2, left ear tube 16 and right ear tube 18 may be seen extending downward from their respective earpieces, 12, 14 in a general conical or C-shape. It is important for these tubes 16, 18 to be constructed of a flexible material, which include large percentages of rubber, cloth and/or plastics. Tubes 16, 18 serve to conduct air up to air tubes 36 as well to conduct electrical power, audio, video and data feeds downward through optional nexus juncture 20. Additionally, tubes 16, 18 further comprise clips 28, which may fasten the device in place when in use or keep it locally secure when not in use. From nexus juncture 20, combined tube 22 carries all merged wires, tubes and lines through insufflator 24. Insufflator 24, which can be mechanically or electrically powered through a battery or wall circuit, provides bursts of increased air pressure through device 10 and into the ear canal, so that changes to the eardrum can be visually measured. In the preferred embodiment of device 10, earpieces 12, 14 further comprise a tympanometer (not shown) which can generate bursts of sound through tiny speakers near tips 30. The sound that is reflected back from the eardrum can then be measured through miniature audio sensors within the tympanometer and transmitted downward past insufflator 24. Results from the tympanometer are usually graphed by a software program to indicate potential ailments to the eardrum and/or surrounding location. Finally, earpieces, 12, 14 may further comprise any variety of digital thermometer known in the art, which are capable of measuring and sending readings down tube 26. Tube 26 can be seen exiting insufflator 24 and entering handheld computer 40 through port 38.

In the preferred embodiment, handheld computer 40 will be a smart phone with various software applications as well as wireless data communication capability, but could easily be envisioned to be a custom dedicated device or other similar functioning device known in the art. Computer 40 comprises a monitor or screen and a virtual or tactile keypad. Alternate embodiments also comprise a speaker, microphone, camera, mouse, output port 42, touch-pad or joystick 44, camera button 50 and light control button 52. Device 10 may optionally have other controls used for operating the thermometer, tympanometer, cameras, data I/O, screen, and/or any associated software.

Figure 3:
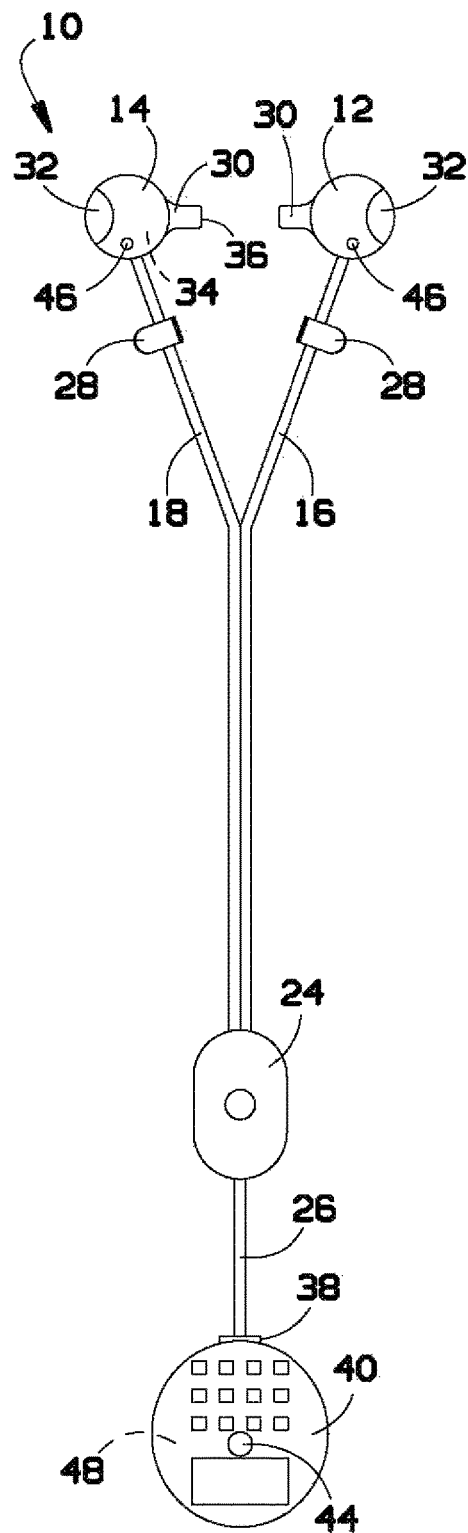
FIG. 3 illustrates a front view of an alternate embodiment of the present invention.

Now referring to FIG. 3, an alternate embodiment of the present disclosure is shown. Device 10 is connected and assembled in a manner so that nexus juncture 20 is absent and tubes, 16, 18 continue straight, but individually to insufflator 24. Tubes, 16, 18 may be intertwined or secured together in some fashion. This construct may allow more flexibility in the operation of device 10. Additionally, insufflator 24 may be attached by separate wire and tubing (not shown) and independently connect tube 26, instead of being positioned between tubes 16, 18 and tube 26.

Figure 4:
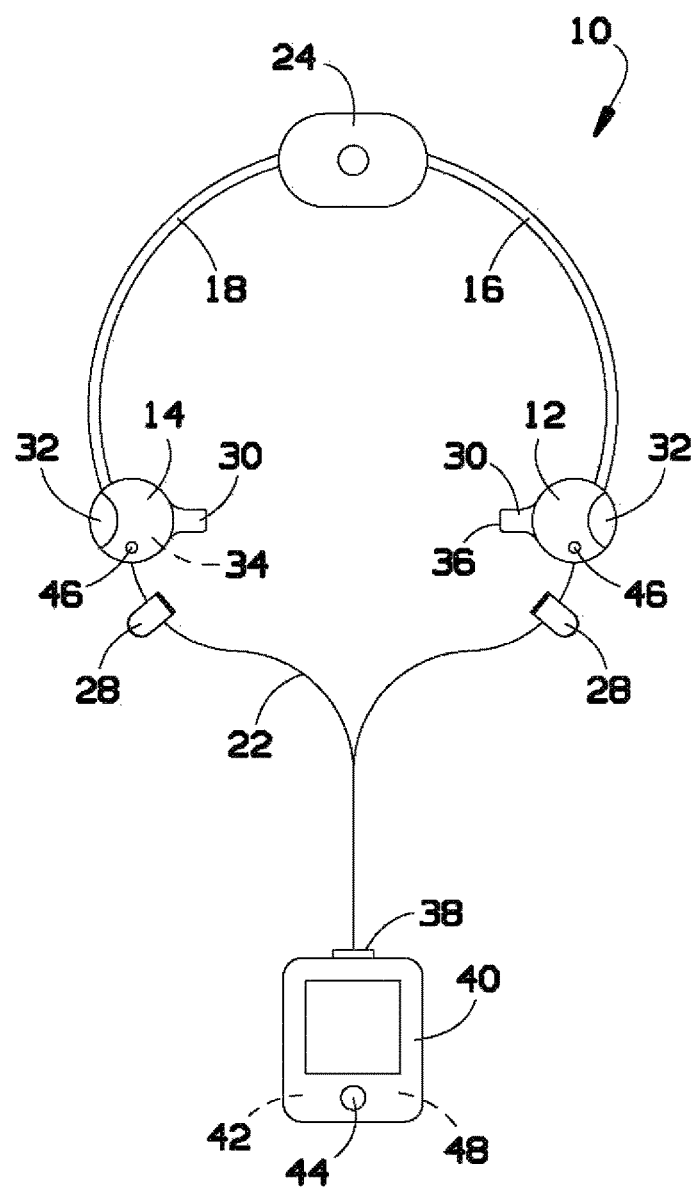
FIG. 4 illustrates a front view of yet another embodiment of the present invention.

Now referring to FIG. 4, another alternate embodiment of the present disclosure is shown with insufflator 24 and tubing 16, 18 opposite computer 40. This version simply shows that tubing (ie. for air) can be kept separate from electrical/data wiring 22. In this configuration, clips 28 can then be placed in alternate locations, such as on electrical/data wiring 22.

The presently disclosed device has a broad range of functionality due to its multiple components. It can provide a visual inspection of a patient's inner ear due to the tips, light source and cameras. It can provide a tactile response in conjunction with the visual inspection due to the insufflator and air tubing. It can also provide a more electronically sensed response due to tiny speakers which emit sound waves and sense reflected sound waves form the tympanometer. This data can only be captured and recorded due to the orientation and construction of the wiring which directly connects to a computerized unit. Finally, temperature within the ear or ears can be simultaneously measured and recorded while any of the previously mentioned tests are being performed. The tests can then be used to diagnose ailments ranging from a build-up of earwax, to an infection to a small perforation in the eardrum or even a misalignment of the ossicles. The versatility of the device eliminates the need for multiple instrumentation. Additionally, the simplicity of the device allows for a user or patient with almost any level of skill, such as a child, to be able to operate the device. The ability to take the various measurements and, in essence, thoroughly examine an ear eliminates the need for a patient to travel to a hospital or be in the presence of a doctor. Instead, a medical practitioner may conduct the diagnosis and prescribe treatment from any remote location.

Figure 5:
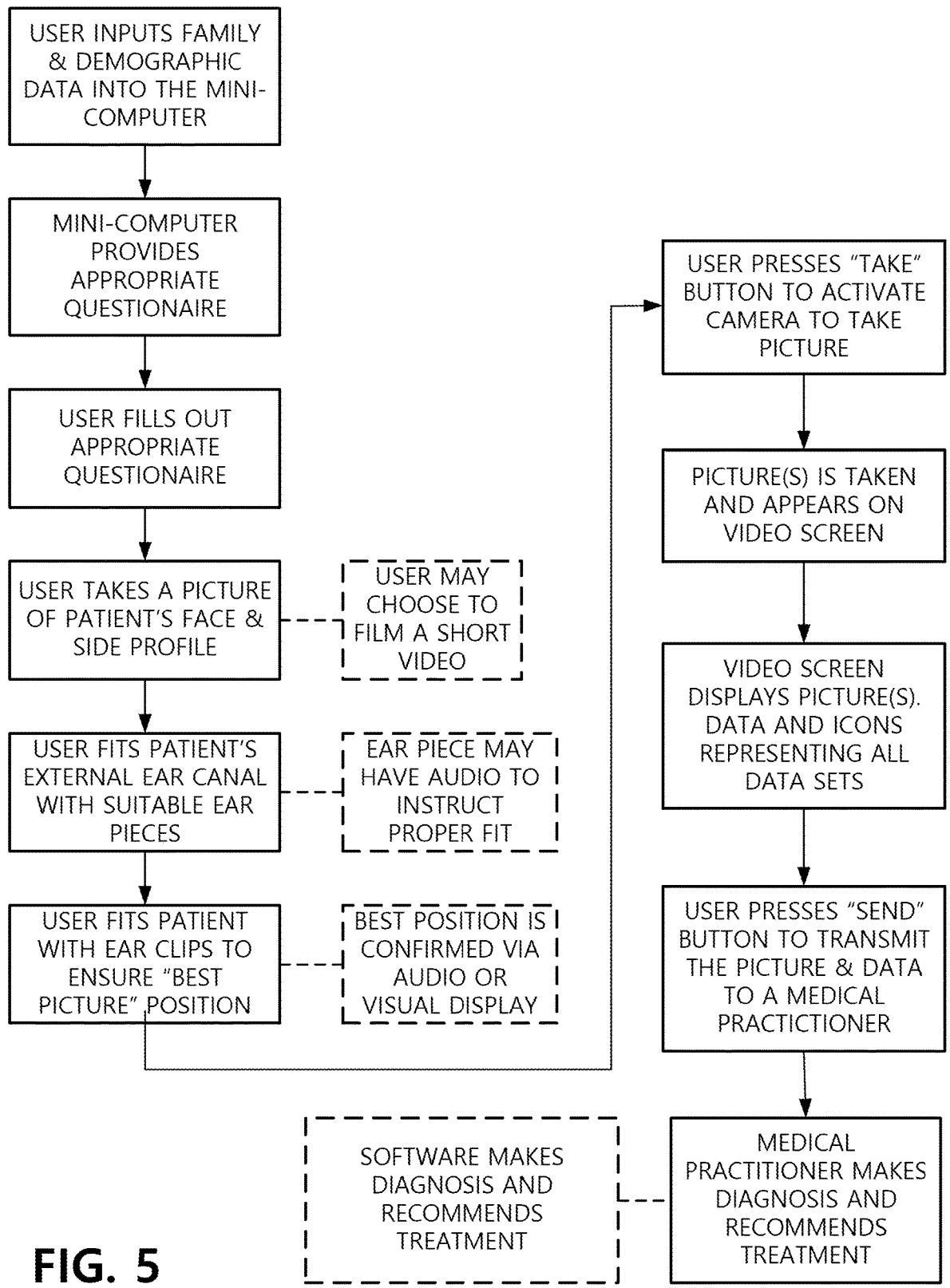
FIG. 5 illustrates a process flow diagram of the preferred embodiment of the method of using the present invention.

Now referring to FIG. 5, a process flow diagram of the preferred method of using the presently disclosed device is shown. First, a user will input family, genetic, demographic and/or past medical record history into the miniature computer. In one embodiment, the computer may then provide an appropriate questionnaire based on this information, which may be helpful in ascertaining additional pertinent information. The user will then fill out this questionnaire, if provided. The user may also take a picture of the outside of the ear and profile of the head. The user will then place at least one tip 30 of earpieces 12, 14 into the external ear canal of their ears. In some circumstances, only one earpiece may be used. In one embodiment of the presently disclosed method, the earpieces may also comprise small speakers which play audio instructions for proper fit of device 10. In the preferred embodiment, the user will also use clips 28 on the pinnea (ear lobe) or external ear in order to ensure the best picture position. The best position can be confirmed via audio or visual display. Once earpieces, 12, 14 are in place, the user may press camera button 50 to activate the cameras to take a picture or video clip. Either the same button, or another button may then be used to adjust the camera settings, including lighting, aperture, focus, and magnification, and "snap" the picture. Additionally, a short video make also be taken. Any number of pictures and video icons will appear on the screen of mini-computer 40. The screen may also display other pictures, data and icons representing all data sets from various tests, various time frames and even various users. The user then sends the pictures and data to a medical practitioner. The medical practitioner makes a diagnosis and recommends a treatment, which is transferred back to the user. In a more sophisticated embodiment of the present device and method, software within the device or located at a remote data center will make the diagnosis and recommend a treatment.

The present invention includes any novel feature or combination of features disclosed herein either explicitly or any generalization thereof. While the invention has been described with respect to specific examples including presently preferred modes of carrying out the invention, those skilled in the art will appreciate that there are numerous variations and permutations of the above described apparatus. Thus, the spirit and scope of the invention should be construed broadly as set forth in the previous specification or appended claims.

What is claimed is:

1. A diagnostic device for optical examination of the outer and middle ear of a patient, the diagnostic device comprising:
    an earpiece shaped to fit in an outer ear of a patient, the earpiece comprising a tip having a length, the length of the tip adjustable, the tip configured to fit into an ear canal of the patient;
    a digital camera included in the earpiece; and
    a light source included in the earpiece.

2. The diagnostic device of claim 1, wherein the tip is flexible.

3. The diagnostic device of claim 1, wherein the length of the tip is extendable.

4. The diagnostic device of claim 1, further comprising a wireless transmitter transmitting data captured by the digital camera to a remote device.

5. The diagnostic device of claim 1, wherein the earpiece comprises a shape configured to fit in and contact the outer visible ear to assist in positioning the diagnostic device.

6. The diagnostic device of claim 1, further comprising a speaker to play instructions or emit an audible confirmation of a desired position.

7. The diagnostic device of claim 1, further comprising a speaker included in the earpiece configured to play instructions or emit an audible confirmation of a desired position.

8. A method for optical examination of an ear canal of a patient, the method comprising:
    positioning the diagnostic device of claim 1 in an outer ear of the patient;
    capturing images of the ear canal using the digital camera;
    illuminating the ear canal using the light source; and
    transmitting data captured by the digital camera to a remote device.

9. The method of claim 8, further comprising extending the length of the tip within the ear canal.

10. The method of claim 8, further comprising extending the length of the tip configured to fit within the ear canal.

11. The method of claim 8, wherein the device further comprises a speaker playing instructions or emitting an audible confirmation of a desired position.

12. The method of claim 8, wherein transmitting data captured by the digital camera comprises wirelessly transmitting the data to the remote device.

13. A system for remote ear examination and diagnosis, comprising:
    a diagnostic device; and
    a remote server in communication with the diagnostic device;
    the diagnostic device comprising:
        an earpiece shaped to fit in an outer ear of a user, the earpiece having a shape configured to contact the outer ear to assist the user in positioning the diagnostic device;
        a digital camera to capture images of the patient's ear canal and middle ear;
        a light source;
        a tip having a length configured to fit into the ear canal of a patient; and
        a processor;
        a memory element storing captured images of the patient's ear canal; and
        a communication interface transmitting the stored images to the remote server;
    the remote server receiving the transmitted images from a base unit, analyzing the received images to identify potential ear ailments, generating a diagnostic report based on the analysis; and
    transmitting the diagnostic report to one of the user, the patient, or a healthcare provider for review.

14. The system of claim 13, where the diagnostic device comprises a smartphone in communication with the earpiece, the smartphone containing a processor, a memory element storing captured images of the patient's ear canal, and the communication interface transmitting the stored images to the remote server.

15. The system of claim 13, where the length of the tip configured to fit within the ear canal is adjustable.

16. The system of claim 13, wherein the earpiece comprises a shape configured to fit in and contact the outer visible ear to assist the user in positioning the diagnostic device.

17. The system of claim 13, further comprising a speaker to play instructions or emit an audible sound confirming a desired position.

18. The system of claim 13, where the earpiece comprises a speaker to play instructions or emit an audible sound confirming a desired position.

19. The system of claim 13, where the digital camera is a device connected to the earpiece as an extension.

* * * * *